(12) United States Patent
Ward

(10) Patent No.: US 6,286,375 B1
(45) Date of Patent: Sep. 11, 2001

(54) APPARATUS FOR FACILITATING HEADSPACE SAMPLING

(75) Inventor: Clyde Ward, Bolverde, TX (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/301,385

(22) Filed: Apr. 27, 1999

(51) Int. Cl.[7] .................................................. G01N 33/27
(52) U.S. Cl. ..................... 73/863.12; 73/19.09; 73/23.41; 73/863.81
(58) Field of Search ............................ 73/863.81, 863.82, 73/863.83, 863.84, 863.85, 863.86, 863.11, 864.81, 864.85, 864.86, 864.87, 23.2, 23.41; 422/100, 101, 83; 436/61, 178

(56) References Cited

U.S. PATENT DOCUMENTS

| 3,365,951 | * | 1/1968 | Jentzsch et al. ......................... 73/422 |
| 3,408,793 | * | 11/1968 | Frazer ..................................... 55/197 |
| 3,475,964 | * | 11/1969 | Jenkins ..................................... 73/422 |
| 3,849,070 | * | 11/1974 | Garza et al. ........................ 23/230 R |
| 4,000,654 | * | 1/1977 | Harris, Jr. ......................... 73/422 CG |
| 4,887,472 | * | 12/1989 | Jansen ................................ 73/863.86 |
| 5,363,707 | * | 11/1994 | Augenblick et al. ............. 73/864.84 |
| 5,396,812 | * | 3/1995 | Peterson ............................ 73/863.81 |
| 5,432,098 | * | 7/1995 | Wilks .................................... 436/178 |
| 5,447,077 | * | 9/1995 | Lautenschlager ................ 73/863.11 |
| 5,567,887 | * | 10/1996 | Schleisman et al. ............. 73/863.12 |
| 5,578,495 | * | 11/1996 | Wilks .................................... 436/178 |
| 5,611,844 | * | 3/1997 | Troost et al. ............................. 95/82 |
| 5,714,676 | * | 2/1998 | Hase ..................................... 73/23.41 |
| 5,762,877 | * | 6/1998 | Brewer .................................... 422/100 |
| 5,792,423 | * | 8/1998 | Markelov .................................. 422/83 |
| 5,976,468 | * | 11/1999 | Godec et al. ........................... 422/100 |
| 5,998,217 | * | 12/1999 | Rao et al. ............................. 436/179 |
| 6,094,998 | * | 8/2000 | Giannone ............................ 73/863.86 |
| 6,098,471 | * | 8/2000 | Berndtsson et al. .............. 73/864.87 |
| 6,146,895 | * | 11/2000 | Green et al. ............................ 436/47 |

* cited by examiner

Primary Examiner—Hezron Williams
Assistant Examiner—Charles D. Garber
(74) Attorney, Agent, or Firm—Tony Y Cole; Bobby D. Scearce; Thomas L. Kundert

(57) ABSTRACT

An apparatus for facilitating vapor extraction from the headspace of a septum-sealed vial containing a sample to be analyzed. The vial is heated, driving dissolved volatile organics out of solution and into the vapor headspace. A first end of a hollow probe penetrates the septum of the sample vial and is submerged within the sample. The second end of the probe is connected to the first port of a two-port gas-tight valve. A first end of a flexible tube is connected to the second port of the valve. The second end of the tube is submerged in a heated liquid source. In one embodiment, the vapor is extracted from the vial through the septum by a vapor extraction means. During vapor extraction, the valve is opened, thereby connecting the vial to the heated liquid via the tube, thereby allowing the liquid to replace the vapor as it is extracted for analysis from the otherwise closed headspace volume. In an alternate embodiment, the heated liquid source is pressurized. During pressurization, the valve is opened, thereby connecting the vial to the heated liquid via the tube. The liquid expels the vapor which may be analyzed.

5 Claims, 3 Drawing Sheets

US 6,286,375 B1

APPARATUS FOR FACILITATING HEADSPACE SAMPLING

RIGHTS OF THE GOVERNMENT

The invention described herein may be manufactured and used by or for the Government of the United States for all governmental purposes without the payment of any royalty.

FIELD OF THE INVENTION

The present invention relates generally to headspace sampling apparatus and, more particularly, to a field usable apparatus for facilitating the extraction of vapor from the headspace of a vial containing a sample of water or soil to be analyzed for volatile contamination.

BACKGROUND OF THE INVENTION

Volatile organic compounds (VOC) in water and soil are routinely analyzed by headspace analysis. A sample of water or soil mixed with water partially fills a closed septum vial and is heated, driving dissolved volatile organics out of solution and into the vapor headspace and establishing an equilibrium between the sample and the vapor. A portion of this vapor is then extracted for analysis by, typically, a form of gas chromatography. Sufficient vapor is extracted from the headspace to purge connecting lines to the gas chromotagraph with a representative sample. Sampling vapor avoids the introduction of non-volatile or solid particles into the inlet of the gas chromatograph, which is not desirable.

Known in the art are field-portable gas chromatograph/mass spectrometers (GC/MS) engineered specifically for on-site VOC analysis. These self-contained devices typically comprise a vacuum system, analytical components and power components within one compact unit and are capable of acquiring and analyzing VOC samples in the field, thus eliminating the problems associated with conventional collecting, shipping, storing, and analyzing of samples. The ability of such portable devices to provide confirmatory test results immediately on site make them particularly useful for hazardous-waste site investigations, and emergency response situations.

Unfortunately, these portable GC/MS devices do not work well in headspace analysis. Their sample vacuum pumping systems are not powerful enough to extract vapors from a headspace. In order to make the portable devices suitable for headspace analysis, portable device manufacturers have developed auxiliary equipment. Such equipment generally operates to replace the headspace vapor with a VOC-free make up gas as the vapor is extracted by the sample pumping system. This additional equipment is complex in operation and expensive.

It is therefore a feature of the present invention to provide a compact portable, apparatus which facilitates the extraction of vapor from the headspace of a sample vial for accurate VOC analysis. An advantage of the invention is the provision of a relatively simple and inexpensive apparatus for facilitating vapor extraction.

A further advantage of the present invention is that it facilitates the extraction of the entire headspace from sample vial, thus increasing the sensitivity of the analysis.

Other aspects and advantages of the invention are set forth in part herein and in part will be obvious herefrom, or may be attained by means of instrumentalities and combinations pointed out in the appended claims.

SUMMARY OF THE INVENTION

In accordance with the foregoing principles and objects of the invention, an apparatus for facilitating vapor extraction from the headspace of a closed septum vial containing a sample to be analyzed is described. The sample vial is exposed to a heat source, thus driving dissolved volatile organics out of solution and into the vapor headspace. The sample vial may be substantially submerged in a heated water bath or sand bath or inserted into the well of a block heater. A first end of a hollow probe penetrates the septum of the sample vial and is submerged within the sample. The second end of the probe is connected to the first port of a two-port gas-tight valve. A first end of a flexible tube is connected to the second port of the valve. The second end of the tube is submerged in a heated liquid reservoir. The liquid is exposed to atmospheric pressure. If the sample vial is submerged in a heated water bath, the second end of the tube is submerged in the water bath. If the sample vial is inserted into a heated sand bath or block heater, the second end of the tube is submerged in heated liquid contained in a second vial. The vapor is extracted from the vial through the septum by a vapor extraction means.

In a first embodiment, vapor is extracted from the headspace, thereby lowering the pressure within the vial and creating a vacuum therein. During such vapor extraction, the valve is opened, thereby connecting the sample in the vial to the liquid, that is, the water from the water bath or liquid in the second vial, via the tube. The liquid thereby replaces the vapor as it is extracted for analysis from the otherwise closed headspace volume. The apparatus thus allows liquid displacement to relieve the vacuum in the headspace of the sample vial during vapor extraction without diluting the vapor.

In an alternate embodiment, the sample vial is inserted into the well of a block heater. As before, a first end of a hollow probe penetrates the septum of the sample vial and is submerged within the sample. The second end of the probe is connected to the first port of a two-port gas-tight valve. A first end of a flexible tube is connected to the second port of the valve. The second end of the tube penetrates the septum of a septum-sealed second vial containing a heated liquid and is submerged in the liquid. A source of pressurized VOC-free gas supplies the gas to the second vial through the septum. During such pressurization, the valve is opened, thereby connecting the vial to the heated liquid via the tube. The heated liquid thereby expels the headspace vapors, which may then be analyzed.

BRIEF DESCRIPTION OF THE DRAWINGS

The invention will be clearly understood from the following detailed description of preferred embodiments thereof read in conjunction with the accompanying drawing wherein.

DETAILED DESCRIPTION OF THE PREFERRED EMBODIMENTS

Figure 1:
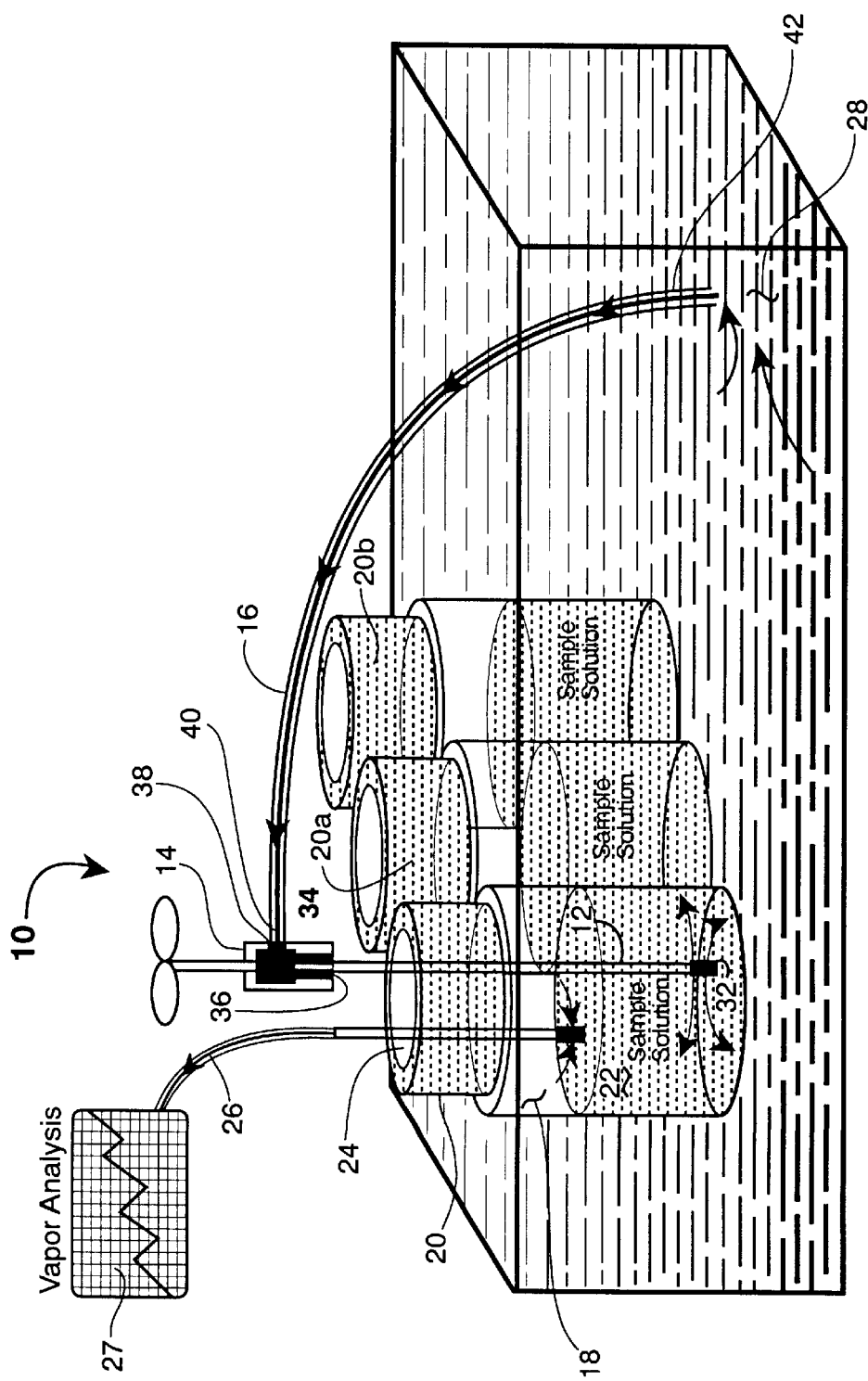
FIG. 1 is a drawing of the essential components of a representative apparatus of the invention in which the sample vial is substantially submerged in a water bath.

Referring now to FIG. 1, shown therein is a drawing of the essential components of an apparatus 10 for facilitating headspace sampling. Sampling apparatus 10 includes a hollow needle probe 12 fitted with a gas-tight valve 14 connecting to a piece of flexible tube 16. As will be fully explained, the invention is used to facilitate the extraction of vapor from the headspace 18 of a vial 20 which contains a sample 22 to be analyzed and which is sealed by a self-sealing septum 24. Septum 24 allows penetration by a probe or needle and forms a gas tight seal around the penetrating probe or needle. As shown in FIG. 1, vapor is extracted from vial 20 through septum 24 by a vapor extraction means 26 and directed to a gas chromatograph or other analytical instrument 27 for analysis. The analytical instrument may be a portable gas chromatograph which includes a vacuum pump for extracting vapor (vapor extraction means), such as the Hapsite™ portable GC/MS manufactured by Inficon Leybold. The vapor extraction means and analytical instrument are not claimed as part of the invention, but description thereof is included to better enable understanding of the invention.

In operation, vial 20 is exposed to a heat source in order to drive dissolved volatile organics out of solution and into the vapor headspace. The heat source may consist of a water bath 28, as shown in FIG. 1. A suitable heat source is the Fisons Haake model W19 water bath. It is obvious that water bath 28 is exposed to atmospheric pressure. Water bath 28 should preferably be heated to 80 degrees F. Vial 20 is placed in a vial holder (not shown) which is positioned in heated water bath 28 such that headspace 18 is substantially submerged. Keeping headspace 18 substantially submerged in the heated water ensures that volatiles will not dissolve back into solution but remain in the vapor headspace.

The first end 32 of probe 12 is positioned so that it penetrates septum 24 and is submerged within sample 22. A 7.75 inch sample needle manufactured by Tekmar-Dohrmann, one end of which should be sharpened for penetrating septum 24, may be used for probe 12. The second end 34 of probe 12 which extends above vial 20 is connected in communication with the first port 36 of two-port valve 14. The second port 38 of valve 14 is connected in communication with the first end 40 of tube 16. A 3-port assembly sample valve manufactured by Tekmar-Dohrmann, one port of which should be sealed and unused, may be used for valve 14. The second end 42 of tube 16 is submerged in water bath 28. Tube 16 may be composed of tygon or a similar material. Next, vapor is extracted through septum 24 from the headspace 18 of vial 20 by vapor extraction means 26, thereby lowering the pressure within vial 20. During this vapor extraction, valve 14 is opened, thereby connecting vial 20 to water bath 28 via tube 16 and probe 12. Valve 14 may be controlled manually or be automated means. In response to the lowering pressure in vial 20, water from water bath 28 flows through tube 16 into probe 12 and thus into vial 20. This water thus replaces the vapor as it is extracted for analysis from the otherwise closed headspace 18, making continued extraction easier. Because water from water bath 28 is heated, it will not cool vial 20 thereby avoiding problems caused by volatiles dissolving back into solution. As illustrated in FIG. 1, vapor extraction may be accomplished in a similar manner from other sample vials 20a and 20b positioned in heated water bath 28.

Figure 2:
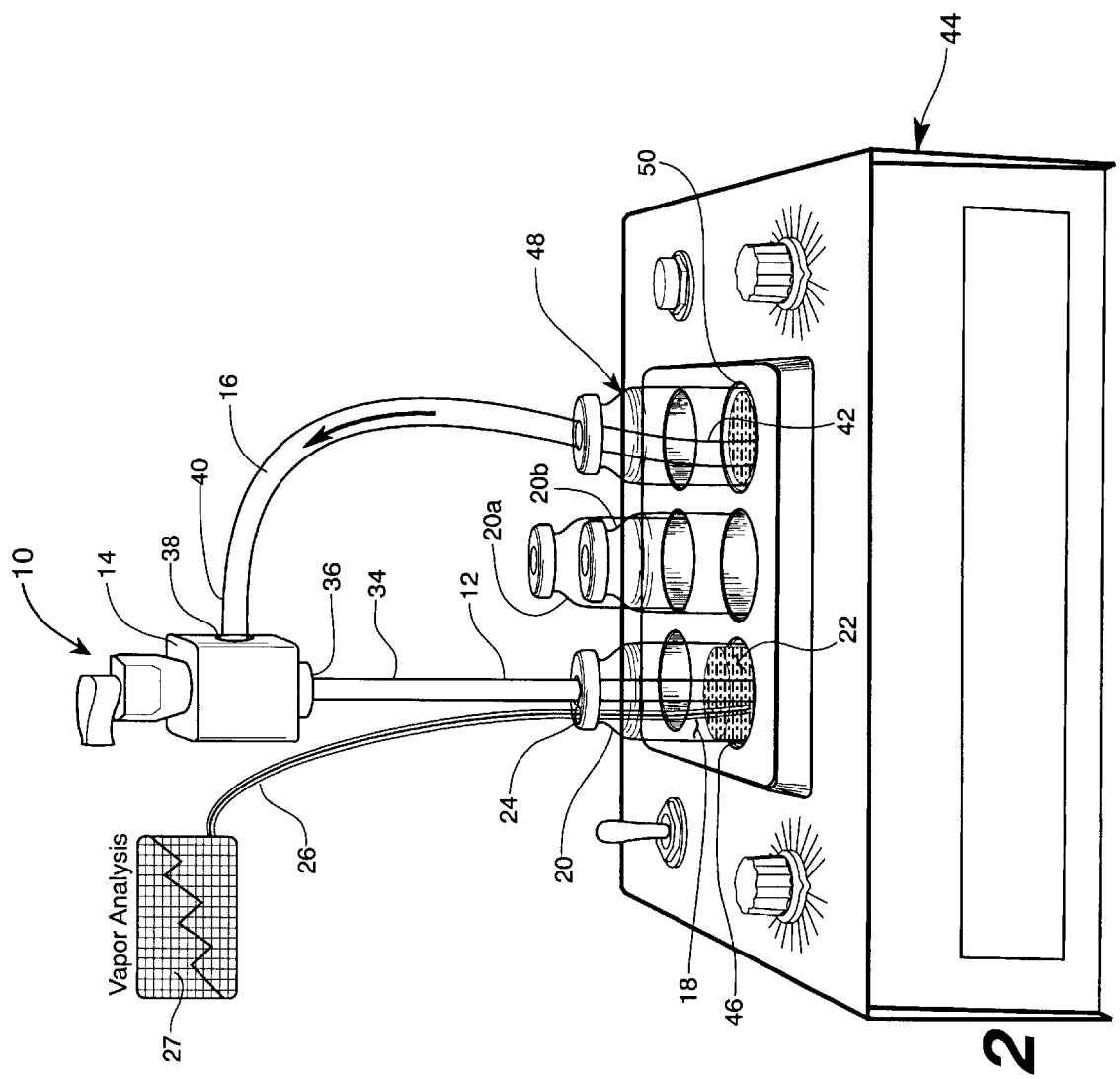
FIG. 2 is a drawing of the essential components of a representative apparatus of the invention in which the sample vial is substantially submerged in the well of a block heater and a second vial substantially submerged in a second well provides a source of heated liquid.

As shown in FIG. 2, an alternative heat source is a block heater 44, such as the Blok Heater™ 33315 manufactured by Supelco of Bellefonte, Pa. In operation, vial 20 is placed in the well 46 of block heater 44, which is preferably heated to 80 degrees F. Well 46 should be deep enough so that headspace 18 is substantially submerged within heated well 46. Keeping headspace 18 substantially submerged in well 46 ensures that headspace 18 remains heated so that volatiles will not dissolve back into solution but remain in the vapor headspace 18. A second vial 48 containing a liquid such as water is placed in a second well 50 of block heater 44. Second vial 48 is not sealed, but open to atmospheric pressure.

As before, first end 32 of probe 12 penetrates septum 24 and is submerged within sample 22. Second end 34 of probe 12 extends above vial 20 and is connected to first port 36 of two-port valve 14. The second port 38 of valve 14 is connected to first end 40 of tube 16. Second end 42 of tube 16 is submerged in the liquid (water) in second vial 48.

Vapor is extracted from headspace 18 of sample vial 20 by vapor extraction means 26, thereby lowering pressure in vial 20. During this vapor extraction, valve 14 is opened, thereby connecting vial 20 to water in second vial 48 via tube 16 and probe 12. In response to the lowering pressure in vial 20, water from second vial 48 flows through tube 16 into probe 12 and thus into vial 20. As before, this water thus replaces the vapor as it is extracted for analysis from headspace 18, thereby relieving the vacuum in headspace 18 resulting from vapor extraction. Because liquid in second vial 48 is heated, it will not cool vial 20, thereby avoiding problems caused by volatiles dissolving back into solution. As illustrated in FIG. 2, vapor extraction may be accomplished in a similar manner from other sample vials 20a and 20b positioned in block heater 44.

Other heat sources, such as a heated sand bath, may be used in a similar manner as will be understood by one skilled in the art.

Apparatus 10 thus allows liquid displacement to relieve the vacuum in headspace 18 during vapor extraction without diluting the vapor. By use of the invention, the entire headspace 18 may be extracted easily and quickly from vial 20.

Figure 3:
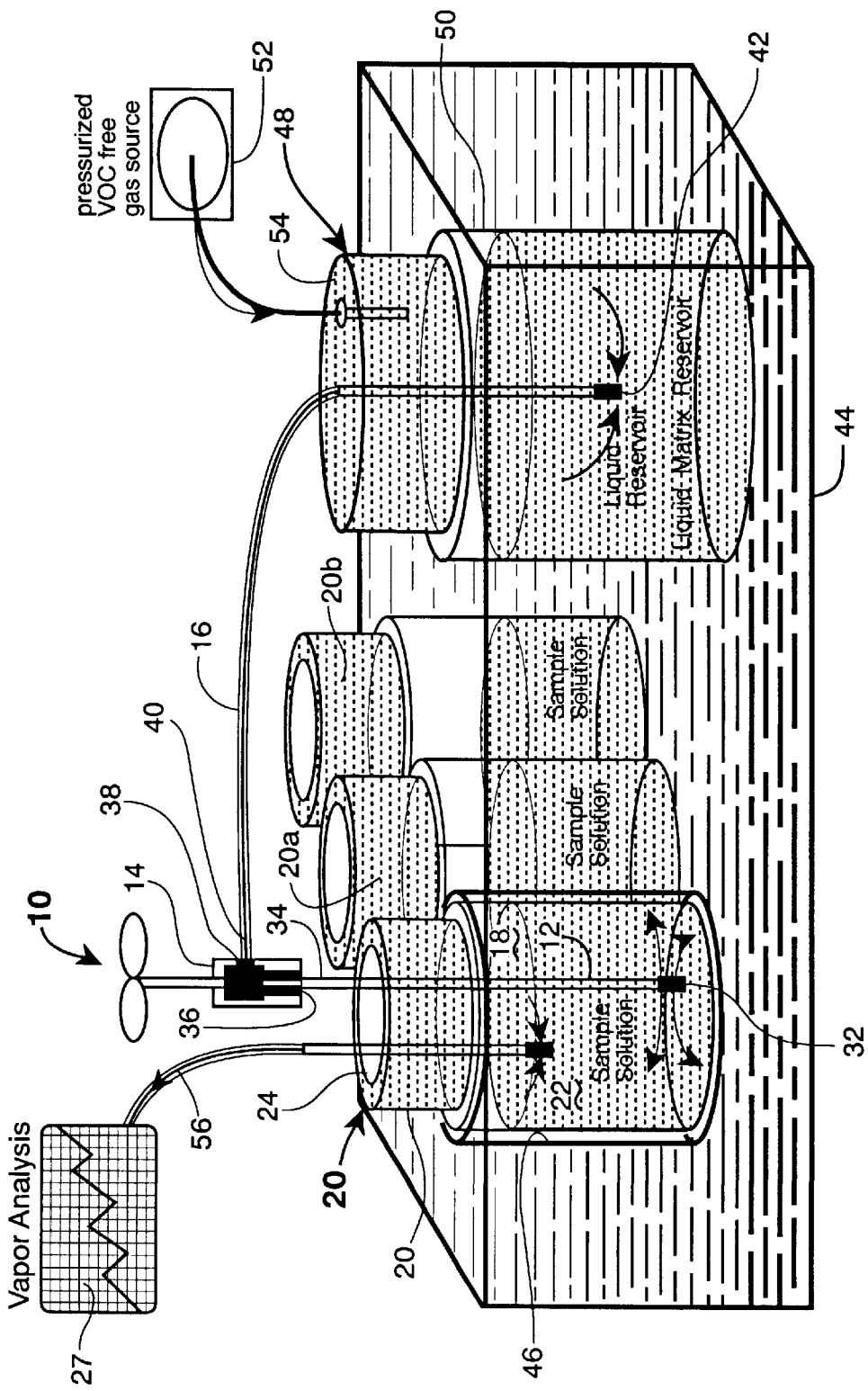
FIG. 3 is a drawing of the essential components of an alternate embodiment of the invention in which the second vial is pressurized by a source of VOC-free gas.

An alternate embodiment of the invention is depicted in FIG. 3. This alternate embodiment includes a source of VOC-free gas 52 for pressurizing second vial 48. This embodiment is usable with analytical instruments that do not use a vacuum system to extract vapors from headspace of sample vial. As before, sample vial 20 is placed in the well 46 of block heater 44, which is preferably heated to 80 degrees F. Second vial 48, which contains a liquid such as water, is placed in a second well 50 of block heater 44. Second vial 48 is sealed by self-sealing septum 54, rather than being open to atmospheric pressure. As before, first end 32 of probe 12 penetrates septum 24 and is submerged within sample 22. Second end 34 of probe 12 extends above vial 20 and is connected to first port 36 of two-port valve 14. The second port 38 of valve 14 is connected to first end 40 of a first tube 16. Second end 42 of tube 16 penetrates septum 54 and is submerged in the liquid (water) in second vial 48. Source 52 supplies pressurized VOC-free gas to second vial 48 through septum 54.

As indicated previously, in the alternative embodiment of FIG. 3, vapor is not extracted from headspace 18 of sample vial 20 by a vapor extraction means. Instead, second vial 48 is pressurized with VOC-free gas by source 52. Source 52 may be a compressed or liquefied gas source with a step-down regulator, a pressure-regulated mechanical pump, or a hand-operated syringe or air pump. During this pressurization, valve 14 is open, thereby connecting vial 20 to water in second vial 48 via tube 16. In response to the increasing pressure in second vial 48, water flows from second vial 48, flows through tube 16 into probe 12 and thus into vial 20. As this water enters vial 20, it expels vapor from headspace 18 through septum 24 into a vapor collection means 56 from which vapors may be directed to analyzing instrument 27. Collection means 56 may be a sample loop, tenex trap or absorbent tube or split column injection. Collection means 56 is not claimed as part of the invention, but description thereof is included to better enable understanding of the invention. As illustrated in FIG. 3, vapor extraction may be accomplished in a similar manner from other sample vials 20a and 20b positioned in block heater 44.

The invention therefore provides a field usable novel apparatus for facilitating the extraction of vapor from a headspace. It is understood that modifications to the invention may be made as might occur to one with skill in the field of the invention within the scope of the appended claims. All embodiments contemplated thereunder that achieve the objects of the invention have therefore not been shown in complete detail. Other embodiments may be developed without departing from the spirit of the invention or from the scope of the appended claims.

What is claimed is:

1. An apparatus for facilitating the extraction of vapor from the headspace of a septum-sealed vial containing a sample of ground water or soil mixed with water to be analyzed for the presence of volatile constituents therein, wherein the vial is placed in a vial holder in a reservoir of heated liquid open to atmospheric pressure thereby driving volatiles in the sample into the vapor headspace, said apparatus comprising:

(a) a hollow needle probe having a first end which may pierce the septum and be submerged into the sample and a second end which may extend above the vial;

(b) a two-port gas-tight valve in communication with said second end of said probe at said first port;

(c) a flexible tube having a first end in communication with said second port of said valve and a second end which may be submerged in the reservoir of heated liquid, whereby, when vapor is extracted through the septum from the headspace, thereby lowering the pressure within the vial and creating a vacuum therein, said valve may be opened thereby connecting the vial to the heated liquid, such that the liquid may flow through said tube into said probe and into said vial in response to the lowering pressure, thereby relieving the vacuum and replacing the extracted vapor.

2. The apparatus of claim 1 in which the heated reservoir is a heated water bath and the sample vial is placed in a vial holder in the water bath such that the headspace is substantially submerged in the water bath.

3. An apparatus for facilitating the extraction of vapor from the headspace of a septum-sealed vial containing a sample of ground water or soil mixed with water to be analyzed for the presence of volatile constituents therein, wherein the vial is placed in the well of a block heater thereby driving volatiles in the sample into the vapor headspace, said apparatus comprising:

(a) a hollow needle probe having a first end which may pierce the septum and be submerged into the sample and a second end which may extend above the vial;

(b) a two-port gas-tight valve in communication with said second end of said probe at said first port;

(c) a flexible tube having a first end in communication with said second port of said valve and a second end which may be submerged in a second vial containing heated liquid and may be submerged in the liquid, wherein the second vial is placed in a second well of the block heater such that the headspace is substantially in the second well and wherein the liquid is open to atmospheric pressure, whereby when vapor is extracted through the septum from the headspace, thereby lowering the pressure within the sample vial and creating a vacuum therein, said valve may be opened thereby connecting the sample vial to the heated liquid, such that the liquid may flow through said tube into said probe and into said sample vial in response to the lowering pressure, thereby relieving the vacuum and replacing the extracted vapor.

4. The apparatus of claim 3 in which the liquid is water.

5. An apparatus for expelling vapor from the headspace of a septum-sealed vial containing a sample of ground water or soil mixed with water to be analyzed for the presence of volatile constituents therein, wherein the vial is placed in the well of a block heater thereby driving volatiles in the sample into the vapor headspace, said apparatus comprising:

(a) a hollow needle probe having a first end which may pierce the septum and be submerged into the sample and a second end which may extend above the vial;

(b) a two-port gas-tight valve in communication with said second end of said probe at said first port;

(c) a flexible tube having a first end in communication with said second port of said valve and a second end which may penetrate the septum of a second septum-sealed vial containing a heated liquid and may be submerged in the liquid, wherein the second vial is placed in a second well of the block heater; and (d) a pressurized VOC-free gas source which may penetrate the septum of the second vial and pressurize the second vial, whereby, when the second vial is pressurized, thereby increasing the pressure within the second vial, said valve may be opened thereby connecting the sample vial to the heated liquid, such that the heated liquid may flow through said tube into said probe and into said sample vial in response to the increasing pressure, thereby expelling the vapor.

* * * * *